United States Patent [19]

Haug et al.

[11] Patent Number: 5,041,609
[45] Date of Patent: Aug. 20, 1991

[54] HERBICIDAL (7-(HETERO) ARYLOXYNAPHTHALEN-2-YL-OXY)-ALKANE-CARBOXYLIC

[75] Inventors: Michael Haug, Bergisch-Gladbach; Roland Andree, Langenfeld; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 246,119

[22] Filed: Sep. 16, 1988

[51] Int. Cl.$^5$ .................. C07C 69/76; A01N 37/36
[52] U.S. Cl. ..................... 560/56; 558/389; 562/466; 71/105; 71/108; 71/114
[58] Field of Search .............. 560/56; 558/389; 562/460

[56] References Cited
FOREIGN PATENT DOCUMENTS 179015 4/1986 European Pat. Off. .
3434447 3/1986 Fed. Rep. of Germany .
165346 7/1986 Japan .
10041 1/1987 Japan .

*Primary Examiner*—Paul J. Killos
*Attorney, Agent, or Firm*—Sprung Horn Kramer et al.

[57] ABSTRACT

Herbicidal compounds of the formula

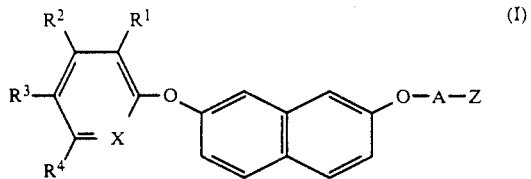

in which
$R^1$ stands for halogen, cyano or trifluoromethyl,
$R^2$ stands for hydrogen or halogen,
$R^3$ stands for halogen, trifluoromethyl, trifluoromethoxy, trifluoromethylthio or trifluoromethylsulphonyl,
$R^4$ stands for hydrogen or halogen,
X stands for nitrogen or for the grouping $C-R^5$,
where
$R^5$ stands for hydrogen or halogen,
with the proviso that at least one of the substituents $R^2$ or $R^4$ is different from hydrogen if $R^1$ stands for chlorine or cyano and simultaneously $R^3$ stands for trifluoromethyl and X stands for CH, and that $R^3$ is different from trifluoromethyl if X stands for nitrogen
A stands for optionally branched alkanediyl, and
Z stands for cyano or the grouping —CO—Y,
where
Y stands for halogen, hydroxyl, amino, alkylamino, alkenylamino, alkinylamino, arylamino, aralkylamino, alkoxycarbonylalkylamino, cyanoamino, dialkylamino, dialkenylamino, N-alkylarylamino, alkylsulphonylamino, arylsulphonlamino, hydroxyamino, alkoxyamino, hydrazino, alkylsulphonylhydrazino, arylsulphonylhydrazino, alkylthio, arylthio, aralkylthio, alkoxycarbonylalkylthio or for the grouping —O—$R^6$.

13 Claims, No Drawings

HERBICIDAL (7-(HETERO) ARYLOXYNAPHTHALEN-2-YL-OXY)-ALKANE-CARBOXYLIC

The invention relates to new (7-hetero)aryloxynaphthalen-2-yl-oxy)-alkanecarboxylic acid derivatives, to processes and new intermediates for their preparation and to their use as herbicides.

It has been already been disclosed that certain dioxybenzene derivatives such as, for example, methyl α-(4-(2,4-dichlorophenoxy)-phenoxy)-propionate (diclofop-methyl), are herbicidally active (cf. DE-OS (German Published Specification) 2,223,894). However, the action of these known compounds against weeds and also their tolerance by crop plants are not always satisfactory.

New (7-(hetero)aryloxynaphthalen-2-yl-oxy)alkanecarboxylic acid derivatives of the general formula (I)

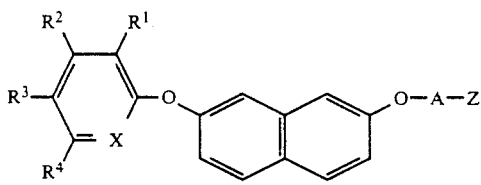

in which
R$^1$ stands for halogen, cyano or trifluoromethyl,
R$^2$ stands for hydrogen or halogen,
R$^3$ stands for halogen, trifluoromethyl, trifluoromethoxy, trifluoromethylthio or trifluoromethylsulphonyl,
R$^4$ stands for hydrogen or halogen,
X stands for nitrogen or for the grouping C—R$^5$, where
R$^5$ stands for hydrogen or halogen,
with the proviso that at least one of the substituents R$^2$ or R$^4$ is different from hydrogen if R$^1$ stands for chlorine or cyano and simultaneously R$^3$ stands for trifluoromethyl and X stands for CH, and that R$^3$ is different from trifluoromethyl if X stands for nitrogen
A stands for optionally branched alkanediyl, and
Z stands for cyano or the grouping —CO—Y, where
Y stands for halogen, hydroxyl, amino, alkylamino, alkenylamino, alkinylamino, arylamino, aralkylamino, alkoxycarbonylalkylamino, cyanoamino, dialkylamino, dialkenylamino, N-alkylarylamino, alkylsulphonylamino, arylsulphonylamino, hydroxyamino, alkoxyamino, hydrazino, alkylsulphonylhydrazino, arylsulphonylhydrazino, alkylthio, arylthio, aralkylthio, alkoxycarbonylalkylthio or for the grouping —O—R$^6$, where
R$^6$ stands for an optionally halogen-substituted radial from the series comprising alkyl, alkenyl, alkinyl, alkoxyalkyl, alkylthioalkyl, alkylsulphinylalkyl, alkylsulphonylalkyl, aryloxyalkyl, aralkoxyalkyl, trialkylsilylalkyl, arylthioalkyl, aralkylthioalkyl, alkoxycarbonylalkyl, alkylaminocarbonylalkyl, arylaminocarbonylalkyl, N-alkyl-N-aryl-aminocarbonylalkyl, aralkyl, azolylalkyl and alkylideneamino, or for an ammonium equivalent, alkylammonium equivalent, alkali metal equivalent or alkaline earth metal equivalent, or for the grouping

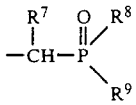

where
R$^7$ stands for hydrogen, alkyl, aryl, furyl, thienyl or pyridyl,
R$^8$ stands for alkyl or alkoxy,
R$^9$ stands for alkoxy and
Q stands for oxygen or sulphur, or
R$^6$ stands for the grouping —(CH$_2$)$_n$—R$^{10}$, where
R$^{10}$ stands for an optionally halogen-substituted and/or optionally alkyl-substituted heterocyclic radical from the series comprising furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, pyridinyl and pyrimidinyl, and
n stands for the numbers 0, 1 or 2, have now been found.

If the new (7-hetero)aryloxynaphthalene-2-yl-oxy)alkanecarboxylic acid derivatives contain asymmetric carbon atoms, the invention relates both to the individual possible isomers and to mixtures of these isomers.

Known compounds have been excepted by the disclaimer established in formula (I) (cf. EP-A-179,015 and JA 62/10041).

Furthermore, it has been found that the new (7-(hetero)-aryloxynaphthalen-2-yl-oxy)-alkanecarboxylic acid derivatives of the formula (I) are obtained when (a) 7-(hetero)aryloxy-2-naphthols of the general formula (II)

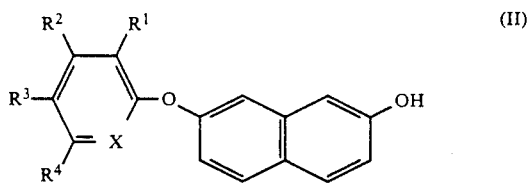

in which
R$^1$, R$^2$, R$^3$, R$^4$ and X have the abovementioned meanings,
are reacted with carboxylic acid derivatives of the general formula (III)

in which
A and Z have the abovementioned meanings and
Z$^1$ stands for a nucleophilic leaving group, if appropriate in the presence of an acid acceptor and if appropriate in the presence of a diluent, or
(b) halogeno-(hetero)aryl compounds of the general formula (IV)

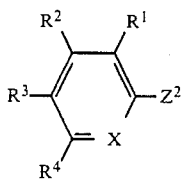

in which

R$^1$, R$^2$, R$^3$, R$^4$ and X have the abovementioned meanings and

Z$^2$ stands for halogen, are reacted with (7-hydroxynaphthalen-2-yl-oxy)-alkanecarboxylic acid derivatives of the general formula (V)

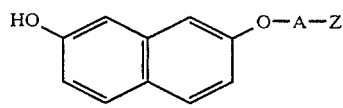

in which

A and Z have the abovementioned meanings, if appropriate in the presence of an acid acceptor and if appropriate in the presence of a diluent, or (c) in the case where in formula (I) Z stands for the grouping —CO—Y, where Y stands for hydroxyl and A, R$^1$, R$^2$, R$^3$, R$^4$ and X have the abovementioned meanings, when compounds of the formula (I) in which Z stands for cyano or for the grouping —CO—Y, where Y stands for methoxy or ethoxy and A, R$^1$, R$^2$, R$^3$, R$^4$ and Y have the abovementioned meanings, are reacted with an alkali metal hydroxide in the presence of an organic solvent, and the reaction mixture is concentrated, if appropriate, and then acidified using a mineral acid, or (d) in the case where in formula (I) Z stands for the grouping —CO—Y, where Y stands for halogen, and A, R$^1$, R$^2$, R$^3$, R$^4$ and X have the abovementioned meanings, when compounds of the general formula (I) in which Z stands for the grouping —CO—Y, where Y stands for hydroxyl and A, R$^1$, R$^2$, R$^3$, R$^4$ and X have the abovementioned meanings, are reacted with a halogenating agent, if appropriate in the presence of a diluent, or (e) in the case where Z in formula (I) stands for the grouping —CO—Y, where Y, halogen excepted, has the above-mentioned meaning and A, R$^1$, R$^2$, R$^3$, R$^4$ and X have the abovementioned meanings, when compounds of the general formula (I), in which Z stands for cyano or the grouping —CO—Y, where Y stands for halogen and A, R$^1$, R$^2$, R$^3$, R$^4$ and X have the abovementioned meanings, are reacted with compounds of the general formula (VI)

H—Y (VI)

in which

Y, halogen excepted, has the abovementioned meaning, if appropriate in the presence of an acid, or an acid acceptor, and if appropriate in the presence of a diluent, or (f) in the case where Z in formula (I) stands for the grouping —CO—Y, where Y stands for the grouping —O—R$^6$, where R$^6$ with the exception of ammonium alkylammonium, alkali metal and alkaline earth metal has the abovementioned meaning and A, R$^1$, R$^2$, R$^3$, R$^4$ and X have the above-mentioned meanings, when compounds of the general formula (I) in which Z stands for the grouping —CO—Y, where Y stands for hydroxyl and A, R$^1$, R$^2$, R$^3$, R$^4$ and Y have the abovementioned meanings, are reacted with compounds of the general formula (VII)

Z$^3$—R$^{6-1}$ (VII)

in which

R$^{6-1}$ with the exception of ammonium, alkylammonium, alkali metal and alkaline earth metal has the abovementioned meaning for R$^6$ and Z$^3$ stands for halogen, if appropriate in the presence of an acid acceptor and if appropriate in the presence of a diluent.

Finally, it has been found that the new (7-(hetero)aryloxynaphthalene-2-yl-oxy)-alkanecarboxylic acid derivatives of the general formula (I) exhibit strong herbicidal properties.

Surprisingly, the (7-hetero)aryloxynaphthalene-2-yl-oxy)-alkanecarboxylic acid derivatives of the formula (I) show considerably a stronger action against problem weeds than methyl α-(4-(2,4-dichlorophenoxy)-phenoxy)propionate, which is a previously known structurally similar active substance of the same type of action, while having a good tolerance by important crop plants.

The carbon chains in the individual radicals such as, for example, alkyl, alkoxy, alkylthio, alkoxyalkyl, alkenyl, alkinyl or alkylsulphinylalkyl, are each straight-chain or branched. The substitution can take place in each case as a monosubstitution or polysubstitution, by identical or different substituents in cases where the radicals are linked by "and/or".

The invention preferably relates to compounds of the formula (I) in which

R$^1$ stands for fluorine, chlorine, bromine, cyano or trifluoromethyl,

R$^2$ stands for hydrogen, fluorine or chlorine,

R$^3$ stands for fluorine, chlorine, bromine, trifluoromethyl, trifluoromethoxy, trifluoromethylthio or trifluoromethylsulphonyl, R$^4$ stands for hydrogen, fluorine or chlorine, X stands for nitrogen or the grouping C—R$^5$, in which R$^5$ stands for hydrogen, fluorine, chlorine or bromine, with the proviso that at least one of the substituents R$^2$ or R$^4$ is different from hydrogen if R$^1$ stands for chlorine or cyano and simultaneously R$^3$ stands for trifluoromethyl and also X stands for CH, and that R$^3$ is different from trifluoromethyl if X stands for nitrogen A stands for optionally branched C$_1$-C$_4$-alkanediyl and Z stands for cyano or the grouping —CO—Y, where Y stands for chlorine, hydroxyl, amino, C$_1$-C$_6$-alkylamino, C$_3$-C$_4$-alkenylamino, C$_3$-C$_4$-alkinylamino, phenylamino, benzylamino, C$_1$-C$_4$-alkoxycarbonyl-C$_1$-C$_2$-alkylamino, cyanoamino, di-(C$_1$-C$_4$-alkyl)-amino, di-(C$_3$-C$_4$-alkenyl)-amino, N-(C$_1$-C$_4$-alkyl)-phenylamino, C$_1$-C$_4$-alkylsulphonylamino, phenylsulphonylamino, tolylsulphonylamino, hydroxyamino, C$_1$-C$_6$-alkoxyamino, hydrazino, C$_1$-C$_4$-alkylsulphonylhydrazino, phenylsulphonylhydrazino, tolylsulphonylhydrazino, C$_1$-C$_4$-alkylthio, phenylthio, benzylthio, C₁-C₄-alkoxy-carbonyl-C₁-C₂-alkylthio, or for the grouping —O—R⁶,
where R⁶ stands for an optionally fluorine-substituted and/or optionally chlorine-substituted radical from the series comprising C₁-C₆-alkyl, C₃-C₄-alkenyl, C₁-C₄-alkinyl, C₁-C₄-alkoxy-C₁-C₄-alkyl, C₁-C₄-alkylthio-C₁-C₄-alkyl, C₁-C₄-alkylsulphinyl-C₁-C₄-alkyl, C₁-C₄-alkylsulphonyl-C₁-C₄-alkyl, phenoxy-C₁-C₃-alkyl, tri(C₁-C₂-alkyl)silyl-C₁-C₂-alkyl, phenylthio-C₁-C₃-alkyl, benzyloxy-C₁-C₃-alkyl, benzylthio-C₁-C₃-alkyl, C₁-C₄-alkoxycarbonyl-C₁-C₂-alkyl, C₁-C₄-alkylaminocarbonyl-C₁-C₄-alkyl, phenylaminocarbonyl-C₁-C₄-alkyl, N-(C₁-C₄-alkyl)-N-phenylaminocarbonyl-C₁-C₄-alkyl, benzyl, pyrazolyl-C₁-C₄-alkyl, C₂-C₄-alkylideneamino or for an ammonium equivalent, a C₁-C₄-alkylammonium equivalent, a sodium equivalent, a potassium equivalent or a calcium equivalent, or for the grouping

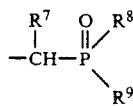

where

R⁷ stands for hydrogen, C₁-C₄-alkyl, phenyl, furyl, thienyl or pyridyl,

R⁸ stands for C₁-C₄-alkyl or C₁-C₄-alkoxy,

R⁹ stands for C₁-C₄-alkoxy and

Q stands for oxygen or sulphur, or

R⁶ stands for the grouping —(CH₂)ₙ—R¹⁰,
where n stands for the numbers 0, 1 or 2, and R¹⁰ stands for a heterocyclic radical which is optionally substituted by fluorine, chlorine, bromine and/or C₁-C₄-alkyl, and which is from the series comprising furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydrophyrrolyl, pyridnyl or pyrimidinyl.

The invention relates in particular to compounds of the formula (I) in which

R¹ stands for fluorine, chlorine or trifluoromethyl,

R² stands for hydrogen, fluorine or chlorine,

R³ stands for chlorine, trifluoromethyl or trifluoromethylsulphonyl,

R⁴ stands for hydrogen, fluorine or chlorine,

X stands for nitrogen or the grouping C-R⁵,
where

R⁵ stands for hydrogen, fluorine or chlorine, with the proviso that at least one of the substituents R² or R⁴ is different from hydrogen if R¹ stands for chlorine and simultaneously R³ stands for trifluoromethyl and X stands for CH, and that R³ is different from trifluoromethyl if X stands for nitrogen A stands for methylene (—CH₂—), dimethylene (—CH₂CH₂—), trimethylene (—CH₂—)₃, ethylidene (—CH—) or propylidene (—CH—)
 |                          |
 CH₃                       C₂H₅

Z stands for cyano or the grouping —CO—Y,
where

Y stands for chlorine, hydroxyl, amino, C₁-C₄-alkylamino, phenylamino, C₁-C₄-alkoxycarbonyl-C₁-C₂-alkylamino, di-(C₁-C₃-alkyl)amino, dialylamino, N-methylphenylamino, C₁-C₄-alkylsulphonylamino, phenylsulphonylamino, hydroxyamino, cyanoamino, C₁-C₄-alkoxyamino, hydrazino, C₁-C₄-alkylsulphonylhydrazino, phenylsulphonylhydrazino, C₁-C₄-alkylthio or C₁-C₄-alkoxycarbonyl-C₁-C₂-alkylthio, or for the grouping —O—R⁶,
where R⁶ stands for C₁-C₄-alkyl, C₁-C₂-alkoxy-C₁-C₂-alkyl, C₁-C₂-alkylthio-C₁-C₂-alkyl, C₁-C₂-alkylsulphinyl-C₁-C₂-alkyl, C₁-C₂-alkylsulphonyl-C₁-C₂-alkyl, benzyloxy-C₁-C₃-alkyl, benzylthio-C₁-C₃-alkyl, C₁-C₄-alkoxycarbonyl-C₁-C₂-alkyl, C₁-C₄-alkylaminocarbonyl-C₁-C₂-alkyl, benzyl, trimethylsilylmethyl or for an ammonium equivalent, C₁-C₃-alkylammonium equivalent, sodium equivalent or potassium equivalent, or for the grouping

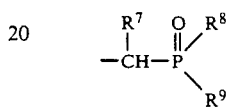

where

R⁷ stands for hydrogen, methyl, phenyl, furyl, thienyl or pyridyl,

R⁸ stands for methoxy or ethoxy,

R⁹ stands for C₁-C₄-alkoxy and

Q stands for oxygen or sulphur or

R⁶ stands for the grouping —(CH₂)ₙ—R¹⁰,
where n stands for the numbers 0, 1 or 2 and R¹⁰ stands for an optionally chlorine-substituted and/or methyl-substituted heterocyclic radical from the series comprising furyl, tetrahydrofuryl, thienyl, perhydropyranyl, oxazolyl, thiazolyl and dioxolanyl.

If, for example, 7-(3,5-dichloropyridin-2-yl-oxy)-2-naphthol and ethyl α-bromopropionate are used as starting substances for process (a) according to the invention, the course of the reaction may be represented by the following equation:

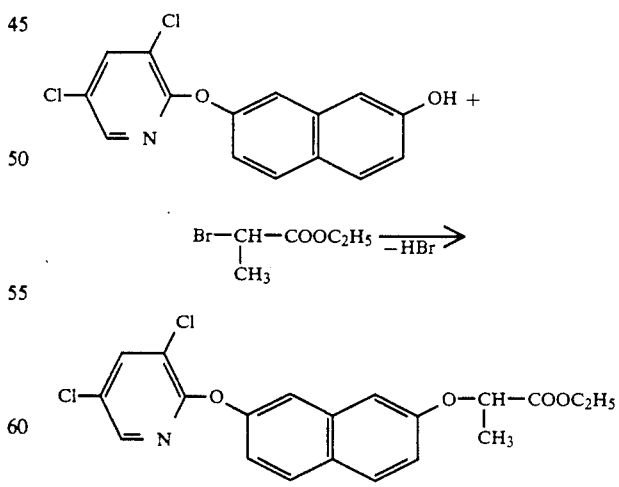

If, for example, 3,4,5-trichlorobenzotrifluoride and butyl (7-hydroxynaphthalen-2-yl-oxy)-acetate are used as starting substances for process (b) according to the invention, the course of the reaction may be represented by the following equation:

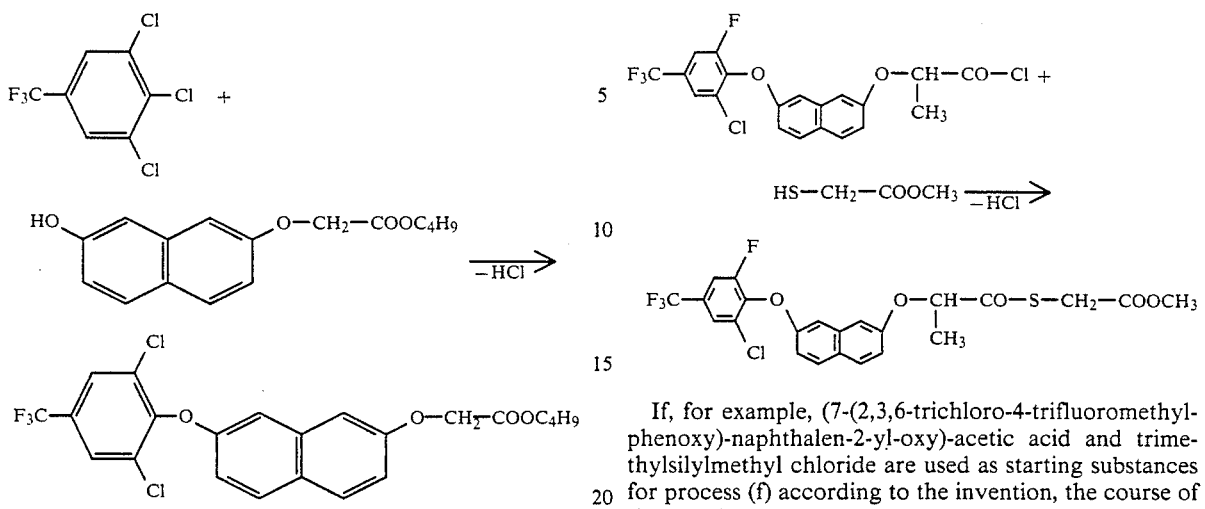

If, for example, methyl β-(7-(3,5-dichloropyridin-2-yl-oxy)-naphthalen-2-yl-oxy)-propionate and sodium hydroxide solution are used as starting substances for process (c) according to the invention, the course of the reaction may be represented by the following equation:

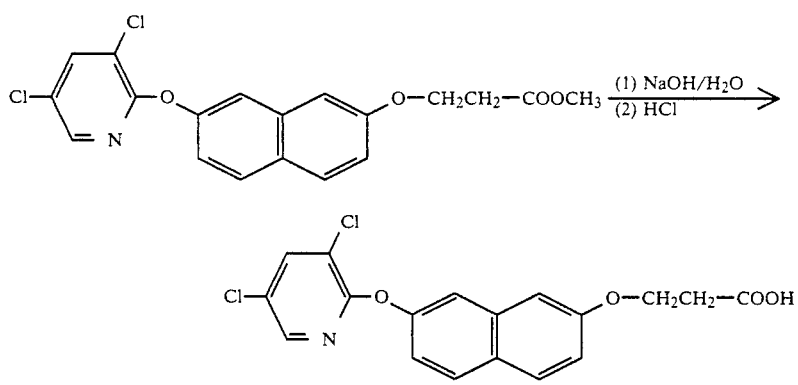

If, for example, α-(7-(2,6-dichloro-3-fluoro-4-trifluoromethyl-phenoxy)-naphthalen-2-yl-oxy)-propionic acid and thionyl chloride are used as starting substances for process (d) according to the invention, the course of the reaction may be represented by the following equation:

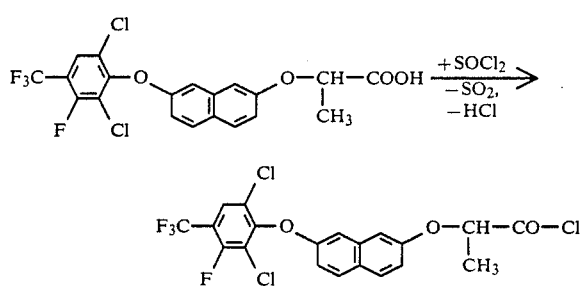

If, for example, α-(7-(2-chloro-6-fluoro-4-trifluoromethylphenoxy)-naphthalen-2-yl-oxy)-propionyl chloride and methyl mercaptoacetate are used as starting substances for process (e) according to the invention, the course of the reaction may be represented by the following equation:

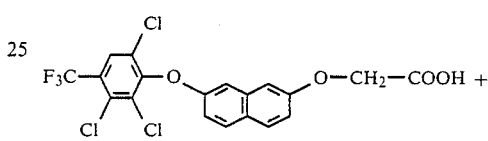

If, for example, (7-(2,3,6-trichloro-4-trifluoromethyl-phenoxy)-naphthalen-2-yl-oxy)-acetic acid and trimethylsilylmethyl chloride are used as starting substances for process (f) according to the invention, the course of the reaction may be represented by the following equation:

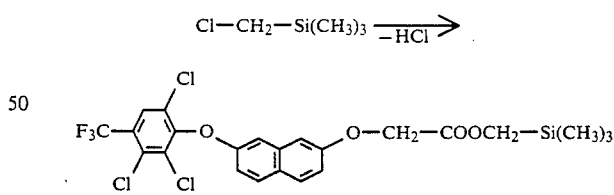

Formula (II) provides a general definition of the 7-(hetero)aryloxy-2-naphthols to be employed as starting substances for process (a) according to the invention for the preparation of compounds of the formula (I).

In formula (II), $R^1$, $R^2$, $R^3$, $R^4$ and X preferably or particularly, have the meanings which have already been described above in connection with the description of the compounds of the formula (I) according to the invention as being preferred, or particularly preferred, respectively for $R^1$, $R^2$, $R^3$, $R^4$ and X.

Examples which may be mentioned of starting substances of the formula (II) are: 7-(2,6-dichloro-4-trifluoromethylphenoxy)-2-naphthol, 7-(2-chloro-6-fluoro-4-trifluoromethylphenoxy)-2-naphthol, 7-(2,6- dichloro-3-fluoro-4-trifluoromethylphenoxy)-2-naphthol, 7-(2,3,6-trichloro-4-trifluoromethylphenoxy)-2-naphthol and 7-(3,5-dichloro-pyridin-2-yl-oxy)-2-naphthol.

Some of the starting substances of the formula (II) have been disclosed in the literature (cf. EP-A 179,015 and JA 62/10041).

7-(Hetero)aryloxy-2-naphthols of the formula (IIa)

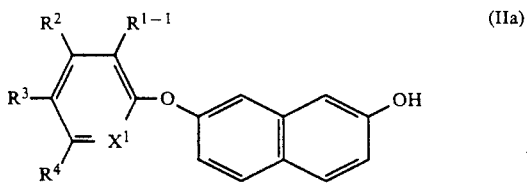

in which $R^{1-1}$ stands for halogen or trifluoromethyl, $R^2$ stands for hydrogen or halogen, $R^3$ stands for halogen, trifluoromethyl, trifluoromethoxy, trifluoromethylthio or trifluoromethylsulphonyl, $R^4$ stands for hydrogen or halogen, and $X^1$ stands for nitrogen or the grouping $C-R^{5-1}$, where $R^{5-1}$ stands for halogen, were hitherto unknown.

The compounds of the formula (IIa) are obtained when appropriate halogeno(hetero)aryl compounds of the formula (IVa)

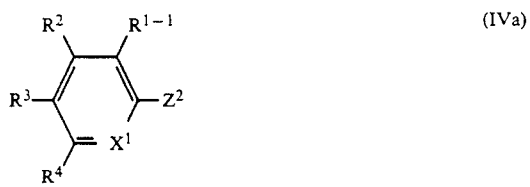

in which $R^{1-1}$, $R^2$, $R^3$, $R^4$, $X^1$ and $Z^2$ have the above-mentioned meanings, are reacted with 2,7-dihydroxynaphthalene in the presence of an acid acceptor such as, for example, sodium hydroxide or potassium hydroxide, and in the presence of a diluent such as, for example, dimethylformamide, dimethylacetamide, dimethylsulphoxide, tetramethylene sulphone or N-methylpyrrolidone, at temperatures between 20° C. and 150° C., and the reaction product is worked up by customary methods.

Preferred compounds of the formula (IIa) are those in which $R^{1-1}$ stands for fluorine, chlorine, bromine or trifluoromethyl, $R^2$ stands for hydrogen, fluorine or chlorine, $R^3$ stands for fluorine, chlorine, bromine, trifluoromethyl, trifluoromethoxy, trifluoromethylthio or trifluoromethylsulphonyl, $R^4$ stands for hydrogen, fluorine or chlorine, and $X^1$ stands for nitrogen or the grouping $C-R^{5-1}$, where $R^{5-1}$ stands for fluorine, chlorine or bromine.

Particularly preferred compounds of the formula (IIa) are those in which $R^{1-1}$ stands for fluorine or chlorine, $R^2$ stands for hydrogen, fluorine or chlorine, $R^3$ stands for chlorine or trifluoromethyl, $R^4$ stands for hydrogen, fluorine or chlorine, and $X^1$ stands for nitrogen or the grouping $C-R^{5-1}$, where $R^{5-1}$ stands for fluorine or chlorine.

Formula (IVa) provides a general definition of the halogeno(hetero)aryl compounds which come under the general formula (IV) to be described further below. In formula (IVa), $R^{1-1}$, $R^2$, $R^3$, $R^4$ and $X^1$ preferably, or particularly, have the meanings which have already been mentioned in connection with the description of the compounds of the formula (IIa) according to the invention as being preferred, or particularly preferred, for $R^{1-1}$, $R^2$, $R^3$, $R^4$ and $X^1$, and $Z^2$ preferably stands for chlorine or fluorine.

Formula (III) provides a general definition of the carboxylic acid derivatives also to be employed as starting substances for process (a) according to the invention. In formula (III), A and Z preferably, or particularly, have the meanings which have already been mentioned above in connection with the description of the compounds of the formula (I) according to the invention as being preferred, or particularly preferred, and $Z^1$ preferably stands for chlorine, bromine, iodine, optionally fluorine-substituted or chlorine-substituted $C_1$-$C_4$-alkylsulphonyloxy, or phenylsulphonyloxy which is optionally substituted by fluorine, chlorine, bromine or methyl, particularly for chlorine, bromine, methylsulphonyloxy, phenylsulphonyloxy or 4-methylphenylsulphonyloxy.

Examples of the compounds of the formula (III) which may be mentioned are: chloroacetonitrile, bromoacetonitrile, β-bromopropionitrile, β-chloropropionitrile, the methyl ester, ethyl ester, propyl ester, isopropyl ester, butyl ester, isobutyl ester and sec.-butyl ester of each of α-chloropropionic acid, α-bromopropionic acid and α-iodopropionic acid, the methyl ester, ethyl ester, propyl ester, isopropyl ester, butyl ester, isobutyl ester and sec.-butyl ester of each of β-chloropropionic acid, β-bromopropionic acid and β-iodopropionic acid, the methyl ester, ethyl ester, propyl ester, isopropyl ester, butyl ester, isobutyl ester and sec.-butyl ester of each of chloroacetic acid, bromoacetic acid and iodoacetic acid, the methyl ester, ethyl ester, propyl ester, butyl ester, isopropyl ester, isobutyl ester and sec.-butyl ester of each of α-methylsulphonyloxypropionic acid, α-ethylsulphonyloxypropionic acid, α-propylsulphonyloxypropionic acid, α-butylsulphonyloxypropionic acid, α-trifluoromethylsulphonyloxypropionic acid, α-phenylsulphonyloxypropionic acid and α-(4-methylphenylsulphonyloxy)-propionic acid.

The starting substances of the formula (III) are known and/or may be prepared by methods known per se (cf. DE-OS (German Published Specification) 2,758,002, DE-OS (German Published Specification) 2,854,542).

Process (a) according to the invention for the preparation of the new compounds of the formula (I) is preferably carried out using diluents. Suitable diluents in this case are virtually all insert organic solvents. These preferably include optionally halogenated aliphatic and aromatic hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and odichlorobenzene, ethers, such as diethyl ether and dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles such as, for example, acetonitrile and propionitrile, amides such as, for example, dimethylformamide, dimethylacetamide and N-methylpyrrolidone and also dimethyl sulphoxide, tetramethylene sulphone and hexamethylphosphoric triamide.

Acid acceptors which may be employed in process (a) according to the invention are all acid-binding agents which can usually be employed for such reactions.

Preferably suitable are alkali metal hydroxides such as, for example, sodium hydroxide and potassium hydroxide, alkaline earth metal hydroxides such as, for example, calcium hydroxide, alkali metal carbonates and alkali metal alkoxides, such as sodium carbonate, potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

When carrying out process (a) according to the invention, the reaction temperatures may be varied within a relatively wide range. In general, the reaction is carried out at temperatures between 0° C. and 150° C., preferably at temperatures between 20° C. and 100° C.

Process (a) according to the invention is generally carried out under atmospheric pressure. However, it is also possible for the process to be carried out under increased or reduced pressure.

For carrying out process (a) according to the invention, 0.5 to 1.2 mols, preferably 0.7 to 1.0 mol, of carboxylic acid derivative of the formula (III) is generally employed per mol of 7-(hetero)aryloxy-2-naphthol of the formula (II). The reaction components are generally mixed together at room temperature or with gentle cooling, and are then stirred—if appropriate at an increased temperature—until the reaction is complete.

Working-up may be carried out in a customary manner. For example, the reaction mixture is stirred or shaken with an acid such as, for example, hydrochloric acid or sulphuric acid and water, and also with an organic solvent which is virtually immiscible with water, such as, for example, methylene chloride or toluene, the organic phase is separated off, washed with water, dried and filtered. The product of the formula (I) which remains in the residue after concentration of the filtrate can be purified in a customary manner, for example, by column chromatography.

Formula (IV) provides a general definition of the halogeno-(hetero)aryl compounds to be employed as starting substances in process (b) according to the invention. In formula (IV), $R^1$, $R^2$, $R^3$, $R^4$ and X preferably, or particularly, have the meanings which have already been mentioned in connection with the description of the compounds of the formula (I) according to the invention as being preferred, or particularly preferred, for $R^1$, $R^2$, $R^3$, $R^4$ and X, and $Z^2$ preferably stands for chlorine or fluorine.

Examples which may be mentioned of the halogeno-(hetero)aryl compounds of the formula (IV) are: 3,4,5-trichlorobenzotrifluoride, 3,4-dichloro-5-fluorobenzotrifluoride, 2,3,4,5-tetrachlorobenzotrifluoride, 3,5-dichloro-2,4-difluorobenzotrifluoride, 3-chloro-4,5-difluorobenzotrifluoride and 2,3,5-trichloropyridine.

The compounds of the formula (IV) are known and/or may be prepared by methods known per se (cf. J. Chem. Soc. 1969, 211–217; ibid. 1971, 1547–1549; EP-A 34,402; U.S. Pat. No. 4,424,396; EP-A 145,314; FR-A 2,538,380 (Chem. Abstracts 102 (1985), 61914x)).

Formula (V) provides a general definition of the (7-hydroxynaphthalen-2-yl-oxy)alkanecarboxylic acid derivatives also to be employed as starting substances for process (b) according to the invention. In formula (V), A and Z preferably, or particularly, have the meanings which have already been mentioned above in connection with the description of the compounds of the formula (I) according to the invention as being preferred, or particularly preferred.

Examples which may be mentioned of the starting substances of the formula (V) are: the nitrile, methyl ester, ethyl ester, propyl ester, isopropyl ester, butyl ester, isobutyl ester and sec-butyl ester of $\alpha$-(7-hydroxynaphthalen-2-yl-oxy)-propionic acid, the nitrile, methyl ester, ethyl ester, propyl ester, isopropyl ester, butyl ester, isobutyl ester and sec-butyl ester of $\beta$-(7-hydroxynaphthalen-2-yl-oxy)-propionic acid, and the nitrile, methyl ester, ethyl ester, propyl ester, isopropyl ester, butyl ester, isobutyl ester and sec-butyl ester of (7-hydroxynaphthalen-2-yl-oxy)-acetic acid.

The starting substances of the formula (V) are known and/or may be prepared by methods known per se (cf. EP-A 179,015).

Process (b) is preferably carried out using a diluent. Suitable diluents are, above all, those which have already been mentioned in the description of process (a) according to the invention. Aprotic polar organic solvents such as, for example, acetone, acetonitrile, methyl ethyl ketone, propionitrile, dimethylformamide, dimethylacetamide, dimethyl sulphoxide, sulpholane and N-methylpyrrolidone are particularly preferred.

Process (b) is preferably carried out in the presence of an acid acceptor. Suitable acid acceptors are, above all, those which have already been mentioned in the description of process (a) according to the invention.

When carrying out process (b) according to the invention, the reaction temperatures may be varied within a relatively wide range. In general, the process is carried out at temperatures between 0° C. and 200° C., preferably at temperatures between 20° C. and 150° C.

Process (b) according to the invention is generally carried out under atmospheric pressure. It is, however, also possible to carry out the process under increased or reduced pressure.

When carrying out process (b) according to the invention, 0.5 to 2 mols, preferably 0.7 to 1.5 mols, of (7-hydroxynaphthalen-2-yl-oxy)-alkanecarboxylic acid derivative of the formula (V) are generally employed per mol of halogeno-(hetero)aryl compound of the formula (IV).

Reaction and working-up may be carried out as described above for process (a).

Formula (I) provides a general definition of the compounds to be employed as starting substances for process (c) according to the invention, with the proviso that Z stands for cyano or the grouping —CO—Y, where Y stands for methoxy or ethoxy. In this case, A, $R^1$, $R^2$, $R^3$, $R^4$ and X preferably, or particularly, have the meanings which have already been mentioned above in the context of the description of the compounds of the formula (I) according to the invention as being preferred, or particularly preferred.

Examples which may be mentioned of the starting substances for process (c) are: the nitrile, methyl ester and ethyl ester of each of α-(7-(3,5-dichloropyridin-2-yl-oxy)-propionic acid, α-(7-(2,6-dichloro-4-trifluoromethylphenoxy)-propionic acid, α-(7-(2-chloro-6-fluoro-4-trifluoromethylphenoxy)-propionic acid, α-(7-(2,3,6-trichloro-4-trifluoromethylphenoxy)-propionic acid and α-(7-(2,6-dichloro-3-fluoro-4-trifluoromethylphenoxy)naphthalen-2-yl-oxy)-propionic acid; the nitrile, methyl ester and ethyl ester of each of β-(7-(3,5-dichloropyridin-2-yl-oxy)-propionic acid, β-(7-(2,6-dichloro-4-trifluoromethylphenoxy)propionic acid, β-(7-(2-chloro-6-fluoro-4-trifluoromethylphenoxy)-propionic acid, β-(7-(2,3,6-trichloro-4-trifluoromethylphenoxy)-propionic acid and β-(7-(2,6-dichloro-3-fluoro-4-trifluoromethylphenoxy)naphthalen-2-yl-oxy)-propionic acid; the nitrile, methyl ester and ethyl ester of each of (7-(3,5-dichloropyridin-2-yl-oxy)-acetic acid, (7-(2-chloro-6-fluoro-4-trifluoromethylphenoxy)-acetic acid, (7-(2,3,6-trichloro-4-trifluoromethylphenoxy)-acetic acid and (7-(2,6-dichloro-3-fluoro-4-trifluoromethylphenoxy)naphthalen-2-yl-oxy)-acetic acid.

The above-described starting substances of the formula (I) for process (c) are new compounds according to the invention; they can be prepared by process (a) or (b) according to the invention.

Process (c) is carried out using alkali metal hydroxides. Examples which may be mentioned for these are lithium hydroxide, sodium hydroxide and potassium hydroxide. Sodium hydroxide is preferably used.

Process (c) is carried out in the presence of water and if appropriate in the presence of an organic solvent. Alcohols such as, for example, methanol or ethanol, are preferably employed as organic solvents.

In process (c), the usual mineral acids such as, for example, hydrochloric acid or sulphuric acid, are used for acidifying.

When carrying out process (c) according to the invention, the reaction temperatures may be varied within a relatively wide range. In general, the process is carried out at temperatures between 10° C. and 150° C., preferably at temperatures between 20° C. and 100° C.

Process (c) according to the invention is normally carried out under atmospheric pressure. However, it is also possible to carry out the process under increased or reduced pressure.

When carrying out process (c), 0.1 to 10 mols, preferably 0.5 to 2 mols, of alkali metal hydroxide are generally employed per mol of starting compound of the formula (I). In general, the reaction components are mixed together at room temperature, and the reaction mixture is stirred until the end of the reaction, if appropriate at an increased temperature. The reaction product which is obtained in the form of crystals can be isolated by filtering with suction, if appropriate, after concentrating, cooling and acidifying the reaction mixture.

Formula (I) provides a general definition for the compounds to be employed as starting substances for process (d) according to the invention, with the proviso that Z stands for the grouping —CO—Y where Y stands for hydroxyl. In this case, A, $R^1$, $R^2$, $R^3$, $R^4$ and X preferably, or particularly, have the meanings which have already been mentioned above in the context of the description of the compounds of the formula (I) according to the invention as being preferred, or particularly preferred.

Examples which may be mentioned of starting substances for process (d) are: α-(7-(3,5-dichloropyridin-2-yl-oxy)-propionic acid, α-(7-(2,6-dichloro-4-trifluoromethylphenoxy)-propionic acid, α-(7-(2-chloro-6-fluoro-4-trifluoromethylphenoxy)-propionic acid, α-(7-(2,3,6-trichloro-4-trifluoromethylphenoxy)-propionic acid and α-(7-(2,6-dichloro-3-fluoro-4-trifluoromethylphenoxy)naphthalen-2-yl-oxy)-propionic acid, β-(7-(3,5-dichloropyridin-2-yl-oxy)-propionic acid, β-(7-(2,6-dichloro-4-trifluoromethylphenoxy)-propionic acid, β-(7-(2-chloro-6-fluoro-4-trifluoromethylphenoxy)-propionic acid, β-(7-(2,3,6-trichloro-4-trifluoromethylphenoxy)-propionic acid and β-(7-(2,6-dichloro-3-fluoro-4-trifluoromethylphenoxy)naphthalene-2-yl-oxy)-propionic acid, (7-(3,5-dichloropyridin-2-yl-oxy)-acetic acid, (7-(2,6-dichloro-4-trifluoromethylphenoxy)-acetic acid, (7-(2-chloro-6-fluoro-4-trifluoromethylphenoxy)-acetic acid, (7-(2,3,6-tri-chloro-4-trifluoromethylphenoxy)-acetic acid and (7-(2,6-dichloro-3-fluoro-4-trifluoromethylphenoxy)naphthalen-2-yl-oxy)-acetic acid.

The abovementioned starting substances of the formula (I) for process (d) are new compounds according to the invention; they can be prepared by process (c) according to the invention.

Process (d) is carried out using a halogenating agent. The customary agents for reacting carboxylic acids to give carboxylic halides may be employed. Examples which may be mentioned here are phosgene, thionyl chloride, phosphoryl chloride and benzotrichloride. Thionyl chloride is preferably used as the halogenating agent.

If appropriate, process (d) is carried out in the presence of a catalyst. The catalysts which are usually employed for the preparation of acid chlorides from acids, such as for example pyridine or dimethylformamide, may be used.

If appropriate, process (d) is carried out in the presence of a diluent. Inert organic solvents from the series comprising the halogenated hydrocarbons, such as, for example, methylene chloride, chloroform, tetrachloromethane or 1,2-dichloroethane, are preferably suitable.

For carrying out process (d) according to the invention, the reaction temperatures may be varied within a relatively wide range. In general, the reaction is carried out at temperatures between 0° C. and 100° C., preferably at temperatures between 10° C. and 90° C.

Process (d) is generally carried out under atmospheric pressure.

When carrying out process (d), 1 to 100 mols, preferably 2 to 50 mols, of halogenating agent are generally employed per mol of starting compound of the formula (I). The reaction components are generally mixed together at room temperature, and the reaction mixture is stirred until the reaction is complete, if appropriate at an increased temperature. The reaction product, which remains after the volatile components have been removed by distillation under reduced pressure, may be purified by recrystallization, or may alternatively be employed in subsequent reactions without further purification.

Formula (I) provides a general definition of the compounds to be employed as starting substances for process (e) according to the invention, with the proviso that Z stands for cyano or the grouping —CO—Y, where Y stands for halogen. In this case, A, $R^1$, $R^2$, $R^3$, $R^4$ and X preferably, or particularly, have the meanings which have already been mentioned above in the context of the description of the compounds of the formula (I) according to the invention as being preferred, or particularly preferred, and Y preferably stands for fluorine, chlorine or bromine, in particular for chlorine.

Examples which may be mentioned of starting substances for process (e) are: α-(7-(3,5-dichloropyridin-2-yl-oxy)-propionyl chloride, α-(7-(2,6-dichloro-4-trifluoromethylphenoxy)-propionyl chloride, α-(7-(2-chloro-6-fluoro-4-trifluoromethylphenoxy)-propionyl chloride, α-(7-(2,3,6-trichloro-4-trifluoromethylphenoxy)-propionyl chloride and α-(7-(2,6-dichloro-3-fluoro-4-trifluoromethylphenoxy)naphthalen-2-yl-oxy)-propionyl chloride; β-(7-(3,5-dichloropyridin-2-yl-oxy)-propionyl chloride, β-(7-(2,6-dichloro-4-trifluoromethylphenoxy)propionyl chloride, β-(7-(2-chloro-6-fluoro-4-trifluoromethylphenoxy)-propionyl chloride, β-(7-(2,3,6-trichloro-4-trifluoromethylphenoxy)-propionyl chloride and β-(7-(2,6-dichloro-3-fluoro-4-trifluoromethylphenoxy)naphthalen-2-yl-oxy)-propionyl chloride; (7-(3,5-dichloropyridin-2-yl-oxy)-acetyl chloride, (7-(2,6-dichloro-4-trifluoromethylphenoxy)-acetyl chloride, (7-(2-chloro-6-fluoro-4-trifluoromethylphenoxy)-acetyl chloride, (7-(2,3,6-trichloro-4-trifluoromethylphenoxy)-acetyl chloride and (7-(2,6-dichloro-3-fluoro-4-trifluoromethylphenoxy)-naphthalen-2-yl-oxy)-acetyl chloride.

The abovementioned starting substances of the formula (I) for process (e) are new compounds according to the invention; they can be prepared by process (d) according to the invention.

Formula (VI) provides a general definition of the compounds also to be employed as starting substances for process (e) according to the invention. In formula (VI), Y preferably, or particularly, has the meaning which has already been mentioned above in connection with the description of the compounds of the formula (I) according to the invention as being preferred, or particularly preferred.

Examples which may be mentioned of starting substances of the formula (VI) are: methylamine, ethylamine, propylamine, isopropylamine, aniline, cyanamide, dimethylamine, diethylamine, hydroxylamine, O-methylhydroxylamine, hydrazine, methylsulphonylhydrazine, methanol, ethanol, propanol, isopropanol, butanol, isobutanol, sec-butanol, 2-methoxyethanol, 2-ethoxyethanol, 2-methylthioethanol, 2-ethylthioethanol, 2-benzyloxyethanol, 3-benzyloxypropanol, 2-benzylthioethanol, the diethyl ester and dimethyl ester of hydroxymethanephosphonic acid, the dimethyl ester and diethyl ester of 1-hydroxyethanephosphonic acid, the dimethyl ester and diethyl ester of 1-hydroxy-1-phenyl-methanephosphonic acid, acetone oxime, 3-hydroxyfuran, furfuryl alcohol, perhydrofurfuryl alcohol, methyl lactate, ethyl lactate, methyl glycolate and ethyl glycolate.

These compounds are known chemicals for synthesis.

Process (e) is preferably carried out using a diluent. Above all, suitable diluents are those which have already been mentioned in the description of process (a) according to the invention.

Process (e) is preferably carried out in the presence of an acid acceptor. Above all, suitable acid acceptors are those which have already been mentioned in the description of process (a) according to the invention.

When carrying out process (e) according to the invention, the reaction temperatures may be varied within a relatively wide range. In general, the reaction is carried out at temperatures between −20° C. and +100° C., preferably at temperatures between 0° C. and 50° C.

Process (e) according to the invention is generally carried out under atmospheric pressure. However, it is also possible to carry out the reaction under increased or reduced pressure.

For carrying out process (e) according to the invention, the starting substances required in each case are generally employed in approximately equimolar amounts. However, it is also possible to use one of the two components employed in each case in excess. The reactions are generally carried out in a suitable diluent in the presence of an acid acceptor, and the reaction mixture is stirred for several hours at the temperature in each case required.

In process (e) according to the invention, working-up is carried out in each case by customary methods. For example, the reaction mixture is diluted with water, if appropriate after the reaction mixture has been concentrated, and the desired reaction product is extracted using an organic solvent which is virtually immiscible with water, for example methylene chloride, chloroform, diethyl ether, toluene or xylene. The organic extraction solution is washed with water, dried using a customary drying agent such as, for example, sodium sulphate, and filtered. After the filtrate has been concentrated, the compounds of the formula (I) are obtained as crude products, which can be purified in a customary manner, for example by chromatography and/or by recrystallization.

Formula (I) provides a general definition of the compounds to be employed as starting substances in process (f) according to the invention with the proviso that Z stands for the grouping —CO—Y, where Y stands for hydroxyl. In this case, A, $R^1$, $R^2$, $R^3$, $R^4$ and X preferably, or particularly, have the meanings which have already been mentioned above in the context of the description of the compounds of the formula (I) according to the invention as being preferred, or particularly preferred.

Examples which may be mentioned of starting substances for process (f) are: α-(7-(3,5-dichloropyridin2-yl-oxy)-propionic acid, α-(7-(2,6-dichloro-4-trifluoromethylphenoxy)-propionic acid, α-(7-(2-chloro-6-fluoro-4-trifluoromethylphenoxy)-propionic acid, α-(7-(2,3,6-trichloro-4-trifluoromethylphenoxy)-propionic acid and α-(7-(2,6-dichloro-3-fluoro-4-trifluoromethylphenoxy)-naphthalen-2-yl-oxy)-propionic acid; β-(7-(3,5-dichloropyridin2-yl-oxy)-propionic acid, β-(7-(2,6-dichloro-4-trifluoromethylphenoxy)-propionic acid, β-(7-(2-chloro-6-fluoro-4-trifluoromethylphenoxy)-propionic acid, β-(7-(2,3,6-trichloro-4-trifluoromethylphenoxy)-propionic acid and β-(7-(2,6-dichloro-3-fluoro-4-trifluoromethylphenoxy)-naphthalen-2-yl-oxy)-propionic acid; (7-(3,5-dichloropyridin-2-yl-oxy)-acetic acid, (7-(2,6-dichloro4-trifluoromethylphenoxy)-acetic acid, (7-(2-chloro-6-fluoro-4-trifluoromethylphenoxy)-acetic acid, (7-(2,3,6-trichloro-4-trifluoromethylphenoxy)-acetic acid and (7-(2,6-dichloro-3-fluoro-4-trifluoromethylphenoxy)-naphthalen-2-yl-oxy)-acetic acid.

The above-described starting substances of the formula (I) for process (f) are new compounds according to the invention; they may be prepared by process (c) according to the invention.

Formula (VII) provides a general definition of the compounds also to be employed as starting substances for process (f) according to the invention. In formula (VII), $R^{6-1}$ preferably stands for $C_1$-$C_6$-alkyl, $C_3$-$C_4$-alkenyl, $C_3$-$C_4$-alkinyl, $C_1$-$C_4$-alkoxy-$C_1$-$C_4$-alkyl, $C_1$-$C_4$-alkylthio-$C_1$-$C_4$-alkyl, phenoxy-$C_1$-$C_3$-alkyl, trimethylsilylmethyl, phenylthio-$C_1$-$C_3$-alkyl, benzyloxy-$C_1$-$C_3$-alkyl, benzylthio-$C_1$-$C_3$-alkyl and $C_1$-$C_4$-alkoxycarbonyl-$C_1$-$C_2$-alkyl, and $Z^3$ preferably stands for chlorine, bromine or iodine.

In formula (VII), $R^{6-1}$ particularly stands for trimethylsilylmethyl and $Z^3$ particularly stands for chlorine.

As a starting compound of the formula (VII) for process (f), trimethylsilylmethyl chloride is particularly preferred.

The starting substances of the formula (VII) are known chemical for synthesis.

Process (f) is preferably carried out using a diluent. Above all, suitable diluents are those which have already been mentioned in the description of process (a) according to the invention. Acetone, acetonitrile and dimethylformamide are particularly preferred Process (f) is preferably carried out in the presence of an acid acceptor. Above all, suitable acid acceptors are those which have already been mentioned in the description of process (a) according to the invention. 1,8-Diazabicyclo-[5.4.0]-undec-7-ene (DBU) is particularly preferred.

When carrying out process (f) according to the invention, the reaction temperature may be varied within a relatively wide range. In general, the reaction is carried out at temperatures between 0° C. and 150° C., preferably at temperatures between 20° C. and 100° C.

Process (f) according to the invention is generally carried out under atmospheric pressure. However, it is also possible to carry out the reaction under increased or reduced pressure.

When carrying out process (f), 1 to 3 mols, preferably 1.1 to 2.5 mols, of starting compound of the formula (VII) are generally employed per mol of starting compound of the formula (I).

Both reaction and working-up may be carried out as described above for process (a).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the Genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are suitable, in particular, for the selective combating of dicotyledon weeds, above all in the post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as finely divided silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable for the mixtures are known herbicides such as, for example, 1-amino-6-ethylthio-3-(2,2-dimethyl-propyl)-1,3,5-triazine-2,4(1H,3H)-dione (amethydione) or N-(2-benzothiazolyl)-N,N'-dimethylurea (metabenzthiazuron) for combating weeds in cereals; 4-amino-3-methyl-6-phenyl-1,2,4-triazin-5(4H)-one (metamitron) for combating weeds in sugar beets, and 4-amino-6-(1,1-dimethylethyl)-3-methylthio-1,2,4-triazin-5(4H)-one (metribuzin) for combating weeds in soy beans, furthermore 2,4-dichlorophenoxyacetic acid (2,4-D); 2,4-dichlorophenoxypropionic acid (2,4-DP); 4-(2,4-dichlorphenoxy) butyric acid (2,4-DB); methyl 5-(2,4-dichlorophenoxy)-2-nitrobenzoate (bifenox); 3,5-dibromo-4-hydroxy-benzo-nitrile (bromoxynil); 2-chloro-N-{[(4-methoxy-6-methyl-1,3,5-triazin-2-yl)-amino]-carbonyl}-benzenesulphonamide (chlorsulfuron); N,N-dimethyl-N'-(3-chloro-4-methyl-phenyl)-urea (chlortoluron); 2-[4-(2,4-dichlorophenoxy)-phenoxy]-propionic acid, its methyl ester or its ethyl ester; 3,6-dichloro-2-pyridinecarboxylic acid (clopyralid); 2-{4-[(6-chloro-2-benzoxazolyl)-oxy]-phenoxy}-propanoic acid, its methyl ester or its ethyl ester (fenoxaprop); its trimethylsilylmethyl 2-[4-(3,5-dichloropyrid-2-yloxy)-phenoxy]-propionate; methyl-2-[4,5-dihydro4-methyl-4-(1-methylethyl)-5-oxo-1H-imidazol-2-yl]-4(5)-methylbenzoate (imazamethabenz); 2-[4,5-dihydro-4-methyl-4-isopropyl-5-oxo-(1H)-imidazol-2-yl]-5-ethyl-pyridine-3-carboxylic acid (imazethapyr); 3,5-diiodo-4-hydroxybenzonitrile (ioxynil); N,N-dimethyl-N'-(4-isopropylphenyl)urea (isoproturon); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (mefenazet); 2-{[[((4-methoxy-6-methyl-1,3,5-triazin-2-yl)-amino)-carbonyl]-amino]-sulphonyl}-benzoic acid or its methyl ester (metsulfuron); N-(1-ethylpropyl)-3,4-dimethyl-2,6-dinitroaniline (pendimethalin); methyl 3-[[[[(4-methoxy-6-methyl-1,3,5-triazin-2-yl)-amino]-carbonyl]-amino]-sulphonyl]-thiophene-2-carboxylate (thiameturon), and also 3,5,6-trichloro-2-pyridyloxyacetic acid (triclopyr).

Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a relatively wide range. It depends essentially on the nature of the desired effect. In general, the amounts used are between 0.01 and 10 kg of active compound per hectare of soil surface, preferably between 0.05 and 15 kg per ha.

The preparation and use of the active compounds according to the invention can be seen from the following examples.

PREPARATION EXAMPLES

Example 1

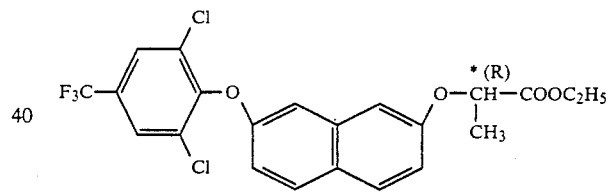

A mixture of 16.8 g (0.045 mol) of 7-(2,6-dichloro-4-trifluoromethylphenoxy)-2-naphthol, 13.6 g (0.050 mol) of ethyl (S)-α-(4-methylphenylsulphonyloxy)propionate, 6.3 g of potassium carbonate and 150 ml of acetonitrile are refluxed for 20 hours. The reaction mixture is cooled to approximately 20° C. and is diluted to approximately twice the volume with water, acidified with 1N hydrochloric acid and shaken with toluene. The organic phase is separated off, washed with water, dried using sodium sulphate and filtered. The solvent is carefully removed from the filtrate by distillation in a water-pump vacuum.

17.6 g (83% of theory) of ethyl (R)-α-(7-(2,6-dichloro-4-trifluoromethylphenoxy)-naphthalen-2-yl-oxy)propionate are obtained in the form of an amorphous residue ($^1$H-NMR (CDCl$_3$): δ C$\underline{H}$CH$_3$=4.8 ppm (q).

The compounds of the formula (I) listed below in Table 1 may be prepared in analogy to Example 1 and in accordance with the general description of the preparation processes.

TABLE 1

Examples of the compounds of the formula (I)

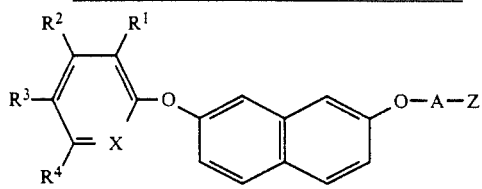

(I)

| Example No. | R¹ | R² | R³ | R⁴ | X | A | Z | Physical data |
|---|---|---|---|---|---|---|---|---|
| 2 | Cl | Cl | CF$_3$ | H | C—Cl | —CH(CH$_3$)— | COOCH$_2$P(O)(OCH$_3$)$_2$ | |
| 3 | Cl | H | Cl | H | N | —CH(CH$_3$)— | COOC$_2$H$_5$ | $n_D^{20}$ = 1,6080 |
| 4 | Cl | H | CF$_3$ | H | C—F | —CH(CH$_3$)— | COOC$_2$H$_5$ | $n_D^{20}$ = 1,5638 |
| 5 | Cl | Cl | CF$_3$ | H | C—Cl | —CH(CH$_3$)— | COOC$_4$H$_9$ | |
| 6 | Cl | F | CF$_3$ | H | C—Cl | —CH(CH$_3$)— | COOCH(CH$_3$)$_2$ | |
| 7 | Cl | H | CF$_3$ | H | C—Cl | —CH$_2$— | COOC$_4$H$_9$ | |
| 8 | Cl | H | CF$_3$ | H | C—Cl | —CH$_2$CH$_2$— | COOCH$_3$ | |
| 9 | Cl | H | CF$_3$ | H | C—Cl | —CH(CH$_3$)— | COOH | M.p.: 138° C. |
| 10 | Cl | H | Cl | H | N | —CH$_2$— | COOH | |
| 11 | Cl | H | Cl | H | N | —CH(CH$_3$)— | COOH | |
| 12 | Cl | H | CF$_3$ | H | C—Cl | —CH$_2$— | COOH | |
| 13 | Cl | H | Cl | H | N | —CH(CH$_3$)— | COCl | |
| 14 | Cl | H | CF$_3$ | H | C—Cl | —CH(CH$_3$)— | COCl | |
| 15 | Cl | H | CF$_3$ | H | C—Cl | —CH(CH$_3$)— | COO—CH$_2$—COOC$_4$H$_9$ | |
| 16 | Cl | H | CF$_3$ | H | C—Cl | —CH(CH$_3$)— | COOCH(CH$_3$)COOC$_2$H$_5$ | |
| 17 | Cl | H | CF$_3$ | H | C—Cl | —CH$_2$— | COOCH(CH$_3$)COOC$_2$H$_5$ | |
| 18 | Cl | Cl | CF$_3$ | H | C—Cl | —CH$_2$— | COSC$_2$H$_5$ | |
| 19 | Cl | F | CF$_3$ | H | C—Cl | —CH(CH$_3$)— | COSCH$_2$COOCH$_3$ | |
| 20 | Cl | H | Cl | H | N | —CH$_2$CH$_2$— | CONHC$_2$H$_5$ | |
| 21 | Cl | H | CF$_3$ | H | C—Cl | —CH$_2$— | COCl | |
| 22 | Cl | H | CF$_3$ | H | C—Cl | —CH$_2$CH$_2$— | COCl | |
| 23 | Cl | H | CF$_3$ | H | C—Cl | —CH$_2$CH$_2$— | COOH | |
| 24 | Cl | H | Cl | H | N | —CH$_2$CH$_2$— | COOH | |

TABLE 1-continued

Examples of the compounds of the formula (I)

| Example No. | R¹ | R² | R³ | R⁴ | X | A | Z | Physical data |
|---|---|---|---|---|---|---|---|---|
| 25 | Cl | H | Cl | H | N | —CH(CH₃)— | COOCH₂CH₂OCH₃ | |
| 26 | Cl | H | CF₃ | H | C—Cl | —CH(CH₃)— | COOCH₂CH₂SC₂H₅ | |
| 27 | Cl | H | Cl | H | N | —CH₂— | COOCH₂—P(O)(OC₂H₅)₂ | |
| 28 | Cl | H | CF₃ | H | C—Cl | —CH₂— | COOCH(C₆H₅)—P(O)(OCH₃)₂ | |
| 29 | Cl | H | CF₃ | H | C—Cl | —CH₂CH₂— | CONHCH(CH₃)₂ | |
| 30 | Cl | Cl | CF₃ | H | C—Cl | —CH₂— | CON(C₂H₅)₂ | |
| 31 | Cl | F | CF₃ | H | C—Cl | —CH(CH₃)— | COOCH₂CH₂OCH₂C₆H₅ | |
| 32 | Cl | H | CF₃ | H | C—F | —CH(CH₃)— | COOCH₂(2-furyl) | |
| 33 | Cl | H | Cl | H | N | —CH₂— | CONHOCH₃ | |
| 34 | Cl | H | CF₃ | H | C—Cl | —CH₂CH₂— | CONHOC₂H₅ | |
| 35 | Cl | Cl | CF₃ | H | C—Cl | —CH(CH₃)— | CONHCH₂COOC₂H₅ | |
| 36 | Cl | H | CF₃ | H | C—Cl | —CH₂— | CONHNHSO₂CH₃ | |
| 37 | Cl | H | Cl | H | N | —CH₂— | COOCH₂Si(CH₃)₃ | |
| 38 | Cl | H | CF₃ | H | C—Cl | —CH(CH₃)— | COO(CH₂)₃OCH₂C₆H₅ | |
| 39 | Cl | H | CF₃ | H | C—Cl | —CH₂— | CN | M.p.: 163° C. |
| 40 | Cl | H | CF₃ | H | C—Cl | —CH₂CH₂— | CN | |
| 41 | Cl | H | Cl | H | N | —CH₂— | CN | |
| 42 | Cl | Cl | CF₃ | H | C—Cl | —CH₂— | CN | |
| 43 | Cl | F | CF₃ | H | C—Cl | —CH₂— | CN | |
| 44 | Cl | H | CF₃ | H | C—F | —CH₂— | CN | |
| 45 | Cl | Cl | CF₃ | H | C—Cl | —CH(CH₃)— | COOC₂H₅ | (amorphous) |
| 46 | Cl | H | CF₃ | H | C—Cl | —CH(CH₃)— (R) | COOCH₃ | M.p.: 89° C. |
| 47 | Cl | H | CF₃ | H | C—Cl | —CH₂CH₂— | COOC₂H₅ | |
| 48 | F | F | CF₃ | F | C—F | —CH(CH₃)— | COOC₂H₅ | |

TABLE 1-continued

Examples of the compounds of the formula (I)

$$\text{(I)}$$

Structure: R¹, R², R³, R⁴ substituted pyridine (with X) linked via O to naphthalene linked via O-A-Z

| Example No. | R¹ | R² | R³ | R⁴ | X | A | Z | Physical data |
|---|---|---|---|---|---|---|---|---|
| 49 | Cl | H | CF$_3$ | H | C—F | —CH(CH$_3$)— | COOH | |
| 50 | Cl | H | CF$_3$ | H | C—F | —CH(CH$_3$)— | COOCH$_2$Si(CH$_3$)$_3$ | |
| 51 | Cl | H | CF$_3$ | H | C—F | —CH(CH$_3$)— | COOCH$_2$P(O)(OC$_2$H$_5$)$_2$ | |
| 52 | Cl | H | CF$_3$ | H | C—Cl | —CH(CH$_3$)— | COOCH$_2$Si(CH$_3$)$_3$ | |
| 53 | Cl | H | CF$_3$ | H | C—Cl | —CH(CH$_3$)— | COOCH$_2$P(O)(OC$_2$H$_5$)$_2$ | |
| 54 | Cl | H | CF$_3$ | H | C—Cl | —CH(CH$_3$)— | COOCH$_2$CH$_2$OC$_2$H$_5$ | |
| 55 | Cl | H | CF$_3$ | H | C—Cl | —CH$_2$— | CO—NH$_2$ | |
| 56 | Cl | H | CF$_3$ | H | C—Cl | —CH$_2$— | CO—N(C$_3$H$_7$)$_2$ | M.p.: 109° C. |
| 57 | Cl | H | CF$_3$ | H | C—Cl | —CH$_2$— | CO—N(CH$_2$CH=CH$_2$)$_2$ | |
| 58 | Cl | H | CF$_3$ | H | C—Cl | (—CH$_2$)$_3$— | COOC$_2$H$_5$ | M.p.: 75° C. |
| 59 | Cl | H | CF$_3$ | H | C—Cl | —CH(C$_2$H$_5$)— | COOC$_2$H$_5$ | M.p.: 118° C. |
| 60 | Cl | H | CF$_3$ | H | C—Cl | —CH(CH$_3$)— | COOCH$_2$-(tetrahydrofuran-2-yl) | |
| 61 | Cl | H | CF$_3$ | H | C—Cl | —CH(CH$_3$)— | COOCH(CH$_3$)P(O)(OCH$_3$)$_2$ | |
| 62 | Cl | H | CF$_3$ | H | C—Cl | —CH$_2$— | COOCH$_3$ | M.p.: 98° C. |
| 63 | Cl | H | CF$_3$ | H | C—Cl | —CH$_2$— | CO—N(CH$_3$)(C$_6$H$_5$) | M.p.: 108° C. |
| 64 | Cl | H | CF$_3$ | H | C—Cl | —CH$_2$— | COOC$_2$H$_5$ | M.p.: 76° C. |
| 65 | Cl | H | SO$_2$CF$_3$ | H | CH | —CH(CH$_3$)— (R) | COOC$_2$H$_5$ | |
| 66 | Cl | H | CF$_3$ | H | C—Cl | —CH(CH$_3$)— (R/S) | COOC$_2$H$_5$ | M.p.: 74° C. |
| 67 | Cl | H | CF$_3$ | F | C—F | —CH(CH$_3$)— | COOC$_2$H$_5$ | |

TABLE 1-continued
Examples of the compounds of the formula (I)

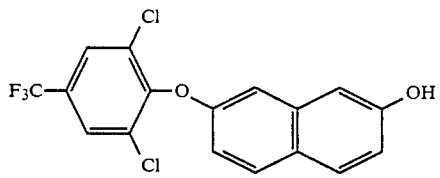

(I)

| Example No. | R¹ | R² | R³ | R⁴ | X | A | | Z | Physical data |
|---|---|---|---|---|---|---|---|---|---|
| 68 | CF₃ | H | CF₃ | H | CH | —CH(CH₃)— | | COOC₂H₅ | |
| 69 | Cl | H | CF₃ | H | C—Cl | —CH(CH₃)— | (S) | COOCH₃ | |
| 70 | CF₃ | H | CF₃ | H | C—Cl | —CH(CH₃)— | (R) | COOC₂H₅ | M.p.: 92° C. |
| 71 | Cl | H | SO₂CF₃ | H | C—Cl | —CH(CH₃)— | (R) | COOC₂H₅ | |
| 72 | Cl | H | CF₃ | H | C—F | —CH(CH₃)— | | COOCH₃ | |
| 73 | Cl | H | CF₃ | H | C—F | —CH₂— | | COOCH₃ | M.p.: 93° C. |
| 74 | Cl | H | CF₃ | H | C—F | —CH(C₂H₅)— | | COOC₂H₅ | |
| 75 | CF₃ | H | CF₃ | H | C—F | —CH(CH₃)— | | COOC₂H₅ | |
| 76 | Cl | H | SO₂CF₃ | H | C—F | —CH₂— | | COOC₂H₅ | viscous oil |

STARTING SUBSTANCES OF THE FORMULA (II)

Example (II-1)

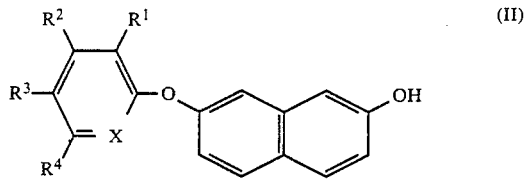

12.5 g (0.05 mol) of 3,4,5-trichloro-benzotrifluoride are added slowly and with stirring to a mixture of 8.0 g (0.05 mol) of 2,7-dihydroxynaphthalene, 4.2 g (0.075 mol) of pulverulent potassium hydroxide and 100 ml of dimethyl sulphoxide, which has been warmed to 60° C., and the reaction mixture is then stirred for a further approx. 3 hours at 60° C. After the mixture has been cooled to approximately 20° C., it is diluted with water and methylene chloride, and filtered. The organic phase is separated off from the filtrate, washed with water, dried using sodium sulphate and filtered. The solvent is removed from the filtrate by distillation in a water-pump vacuum, the residue is stirred with petroleum ether and the product which is thus obtained in the form of crystals is isolated by filtering with suction.

4.9 g (26% of theory) of 7-(2,6-dichloro-4-trifluoromethylphenoxy)-2-naphthol of melting point 98° C. are obtained.

In analogy to Example (II-1) the starting substances of the formula (II) listed below in Table 2 may be prepared.

(II)

TABLE 2
Examples of the starting substances of the formula (II)

| Ex. No. | R¹ | R² | R³ | R⁴ | X | Physical data |
|---|---|---|---|---|---|---|
| II-2 | Cl | Cl | CF₃ | H | C—Cl | |
| II-3 | Cl | F | CF₃ | H | C—Cl | |
| II-4 | Cl | H | CF₃ | H | C—F | M.p.: 91° C. |
| II-5 | Cl | H | Cl | H | N | M.p: 152° C. |

USE EXAMPLES

In the following use examples, the compound mentioned below is used as the comparison substance:

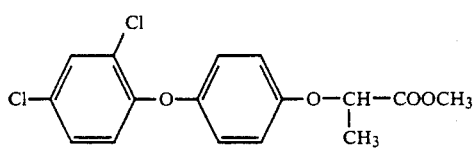

Methyl α-(4-(2,4-dichlorophenoxy)-phenoxy)-propionate (known from DE-OS (German Published Specification) 2,223,894/Compound 86).

EXAMPLE A

Post-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example the compounds of Preparation Examples 1, 4, 73 and 76 show considerably stronger action against problem weeds such as, for example, Amaranthus, Galium, Galinsoga, Ipomoea, Veronica, and Viola, than the comparison substance (A), while having good selectivity in wheat.

It is understood that the specification and examples are illustrative but not limitative of the present invention and that other embodiments within the spirit and scope of the invention will suggest themselves to those skilled in the art.

We claim:

1. A (7-(hetero) aryloxynaphthalen-2-yl-oxy)-alkanecarboxylic acid derivative of the formula

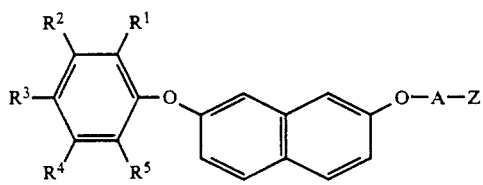

in which
$R^1$ stands for halogen, cyano or trifluoromethyl,
$R^2$ stands for hydrogen or halogen,
$R^3$ stands for halogen, trifluoromethyl, or trifluoromethoxy,
$R^4$ stands for hydrogen or halogen,
$R^5$ stands for halogen,
A stands for optionally branched alkanediyl, and
Z stands for cyano or the grouping —CO—Y;
where
Y stands for halogen, hydroxyl, or for the grouping —O—$R^6$,
where
$R^6$ stands for an optionally halogen-substituted radical from the group consisting of alkyl, alkenyl, alkinyl, alkoxyalkyl, aryloxyalkyl, aralkoxyalkyl, alkoxycarbonylalkyl, alkylaminocarbonylalkyl, N-alkyl-N-aryl-aminocarbonylalkyl, aralkyl.

2. A (7-aryloxynaphthalen-2-yl-oxy)-alkanecarboxylic acid derivative according to claim 1,
in which,
$R^1$ stands for fluorine, chlorine, bromine, cyano or trifluoromethyl,
$R^2$ stands for hydrogen, fluorine or chlorine,
$R^3$ stands for fluorine, chlorine, bromine, trifluoromethyl, or trifluoromethoxy,
$R^4$ stands for hydrogen, fluorine or chlorine,
$R^5$ stands for fluorine, chlorine or bromine.
A stands for optionally branched $C_1$-$C_4$-alkanediyl and
Z stands for cyano or the grouping —CO—Y,
where
Y stands for chlorine, hydroxyl, or for the grouping —O—$R^6$,
where
$R^6$ stands for an optionally fluorine-substituted and/or optionally chlorine-substituted radical from the group consisting of $C_1$-$C_6$-alkyl, $C_3$-$C_4$-alkenyl, $C_3$-$C_4$-alkinyl, $C_1$-$C_4$-alkoxy-$C_1$-$C_4$-alkyl, phenoxy-$C_1$-$C_3$-alkyl, benzyloxy-$C_1$-$C_3$-alkyl, $C_1$-$C_4$-alkoxycarbonyl-$C_1$-$C_2$-alkyl, $C_1$-$C_4$-alkylaminocarbonyl-$C_1$-$C_2$-alkyl, phenylaminocarbonyl-$C_1$-$C_4$-alkyl, N-($C_1$-$C_4$-alkyl)-N-phenylaminocarbonyl-$C_1$-$C_4$-alkyl, benzyl.

3. A compound according to claim 1, wherein such compound is ethyl α-(7-(2,6-dichloro-4-trifluoromethylphenoxy)-naphthalen-2-yl-oxy)-propionate of the formula

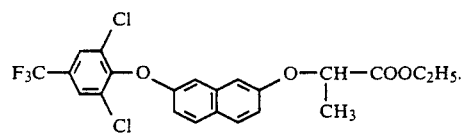

4. A compound according to claim 1, wherein such compound is ethyl α-(7-(2-chloro-6-fluoro-4-trifluoromethylphenoxy)-naphthalen-2-yl-oxy)-propionate of the formula

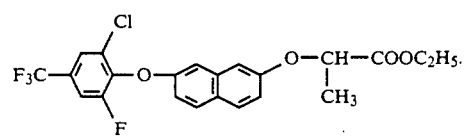

5. A compound according to claim 1, wherein such compound is methyl (7-(2-chloro-6-fluoro-4-trifluoromethylphenoxy)-naphthalen-2-yl-oxy)-acetate of the formula

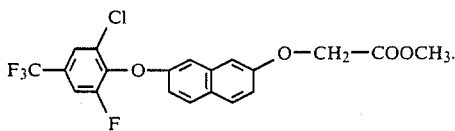

6. A compound according to claim 1, wherein such compound is ethyl (7-(2-chloro-6-fluoro-4-trifluoromethylsulphonyl-phenoxy)-naphthalen-2-yl-oxy)-acetate of the formula

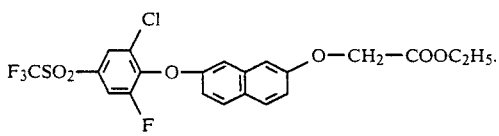

7. A herbicidal composition comprising a herbicidally effective amount of a compound according to claim 1 and a diluent.

8. A method of combating unwanted vegetation which comprises applying to such vegetation or to a locus from which it is desired to exclude such vegetation a herbicidally effective amount of a compound according to claim 1.

9. The method according to claim 8, wherein such compound is
ethyl α-(7-(2,6-dichloro-4-trifluoromethylphenoxy)-naphthalen-2-yl-oxy)-propionate,
ethyl α-(7-(2-chloro-6-fluoro-4-trifluoromethylphenoxy)-naphthalen-2-yl-oxy)-propionate,
methyl (7-(2-chloro-6-fluoro-4-trifluoromethylphenoxy)-naphthalen-2-yl-oxy)-acetate,
ethyl (7-(2-chloro-6-fluoro-4-trifluoromethylsulphonyl-phenoxy)-naphthalen-2-yl-oxy)-acetate or
methyl (7-(2,6-dichloro-4-trifluoromethylphenoxy)-naphthalen-2-yl-oxy)-acetate.

10. A compound according to claim 1, wherein such compound is methyl (7-(2,6-dichloro-4-trifluoromethylphenoxy)-naphthalen-2-yl-oxy)-acetate of the formula

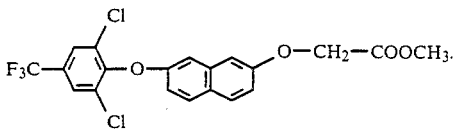

11. A (7-aryloxynaphthalen-2-yl-oxy)-alkanecarboxylic acid derivative according to claim 1, in which
$R^1$ stands for halogen,
$R^2$ and $R^4$ stand for hydrogen,
$R^3$ stands for trifluoromethyl,
A stands for $CH_2$ or $C(CH_3)$,
Z stands for —CO—Y,
Y stands for hydroxyl or —O—$R^6$, and
$R^6$ stands for alkyl.

12. A (7-aryloxynaphthalen-2-yl-oxy)-alkanecarboxylic acid derivative according to claim 11, in which
$R^1$ stands for chlorine,
$R^5$ stands for chlorine or fluorine.

13. A (7-aryloxynaphthalen-2-yl-oxy)-alkanecarboxylic acid derivative according to claim 12, in which
$R^3$ stands for trifluoromethyl.

* * * * *